US007723311B2

(12) United States Patent
Seeney et al.

(10) Patent No.: US 7,723,311 B2
(45) Date of Patent: May 25, 2010

(54) DELIVERY OF BIOACTIVE SUBSTANCES TO TARGET CELLS

(75) Inventors: Charles E. Seeney, Edmond, OK (US); Kenneth J. Dormer, Edmond, OK (US); Richard D. Kopke, Oklahoma City, OK (US)

(73) Assignees: NanoBioMagnetics, Inc.; The University of Oklahoma Hough Ear Institute; The United States of America as represented by the Secretary of the Navy, Washington, DC (US)

( * ) Notice: Subject to any disclaimer, the term of this patent is extended or adjusted under 35 U.S.C. 154(b) by 1393 days.

(21) Appl. No.: 10/871,243

(22) Filed: Jun. 18, 2004

(65) Prior Publication Data

US 2005/0271732 A1 Dec. 8, 2005

Related U.S. Application Data

(60) Provisional application No. 60/479,381, filed on Jun. 18, 2003.

(51) Int. Cl.
*A01N 43/04* (2006.01)
*A61B 5/055* (2006.01)
*A01N 25/26* (2006.01)
*A61F 2/00* (2006.01)
*C12N 15/00* (2006.01)

(52) U.S. Cl. .................. 514/44 R; 424/9.323; 424/417; 424/428; 435/455

(58) Field of Classification Search ............... 514/44 R; 424/9.323, 417, 428; 435/455
See application file for complete search history.

(56) References Cited

U.S. PATENT DOCUMENTS

| 4,501,726 | A | 2/1985 | Schroder et al. ............. 424/1.1 |
|---|---|---|---|
| 4,652,257 | A | 3/1987 | Chang .......................... 604/52 |
| 4,690,130 | A | 9/1987 | Mirell ......................... 128/1.3 |
| 5,916,539 | A | 6/1999 | Pilgrimm |
| 5,928,958 | A | 7/1999 | Pilgrimm |
| 6,014,580 | A * | 1/2000 | Blume et al. ................. 600/424 |
| 6,274,554 | B1 * | 8/2001 | Magal et al. .................. 514/12 |
| 6,344,357 | B1 | 2/2002 | Rickwood |
| 6,436,028 | B1 | 8/2002 | Dormer ........................ 600/25 |
| 6,548,264 | B1 * | 4/2003 | Tan et al. .................... 435/7.21 |
| 6,767,635 | B1 | 7/2004 | Bahr et al. ................... 428/402 |
| 7,189,198 | B2 * | 3/2007 | Harburn et al. ................ 600/9 |
| 2002/0086842 | A1 | 7/2002 | Plank et al. .................... 514/44 |
| 2003/0215394 | A1 * | 11/2003 | Short et al. ................. 424/9.52 |

FOREIGN PATENT DOCUMENTS

| WO | WO 98/01160 | 1/1998 |
|---|---|---|
| WO | WO 99/60998 | 12/1999 |
| WO | WO 02/056890 A1 | 7/2002 |
| WO | WO 03/059194 A2 | 7/2003 |
| WO | WO 2004/006765 | 1/2004 |

OTHER PUBLICATIONS

Caruso et al. Chem. Mater. 13:109-116; 2001.*
Yong Zhang, Nathan Kohler, Miqin Zhang, Surface modification of superparamagnetic magnetite nanoparticles and their intracellular uptake, article, Aug. 8, 2001, Department of Materials Science & Engineering. University of Washington.
Jayanth Panyam, Wen-Zhong Zhou, Swayam Prabha, Sanjeeb K. Sahoo, and Vinod Labhasetwar, Rapid endo-lysosomal escape of poly(DL-lactide-co-glycolide) nanoparticles: implications for drug and gene delivery, article, Apr. 18, 2002, Department of Pharmaceutical Sciences, University of Nebraska Medical Center.
Swayam Prabha, Wen-Zhong Zhou, Jayanth Panyam, Vinod Labhasetwar, Size-dependency of nanoparticle-mediated gene transfection: studies with fractionated nanoparticles, article, Jun. 6, 2002, Department of Pharmaceutical Sciences, University of Nebraska Medical Center.
Chantal A. Lackey, Oliver W. Press, Allan S. Hoffman, and Patrick S. Stayton, A Biomimetic pH-Responsive Polymer Directs Endosomal Release and Intracellular Delivery of an Endocytosed Antibody Complex, article, Jul. 25, 2002, Department of Bioengineering, University of Washington.
C. Wilhelm, C. Billotey, J. Roger, J.N. Pons, J.-C. Bacri, F. Gazeau, Intracellular uptake of anionic superparamagnetic nanoparticles as a function of their surface coating, article, Sep. 9, 2002,Laboratoire des Milieux Desordonnes et Heterogenes, Universite Pierre et Marie Curie, Parris, France.
Jayanth Panyam, Vinod Labhasetwar, Biodegradable nanoparticles for drug and gene delivery to cells and tissue, article, Sep. 16, 2002, Department of Pharmaceutical Sciences, University of Nebraska.
Niren Murthy, Jean Campbell, Nelson Fausto, Allan S. Hoffman, and Patrick S. Stayton, Bioinspired pH-Responsive Polymers for the Intracellular Delivery of Biomolecular Drugs, article, Jan. 15, 2003, Department of Bioengineering and Department of Pathology, University of Washington.
Junghae Suh, Denis Wirtz, and Justin Hanes, Efficient active transport of gene nanocarriers to the cell nucleus, article, Apr. 1, 2003, Departments of Biomedical Engineering, Chemical and Biomolecular Engineering, and Materials Science and Engineering, Molecular Biophysics Program, The Johns Hopkins University, Baltimore, Maryland.

(Continued)

Primary Examiner—Fereydoun G Sajjadi

(57) ABSTRACT

A system for introducing a bioactive substance into a target cell within a body. The bioactive substance is transported to the target cell using a superparamagnetic nanoparticle and a controllable magnetic field generator that is capable of moving the nanoparticle to the target cell through the body in three dimensions. The nanoparticle may be covered with a biocompatible shell that forms a covalent bond with the bioactive substance. In an alternative embodiment, the bioactive substance and a plurality of nanoparticles are supported by a bioerodable matrix that forms a nanosphere. The nanosphere may be moved into the target cell using an external magnetic field that is controllable to move the nanosphere in three dimensions through the body and the bioactive substance is released from the nanosphere once inside the target cell.

19 Claims, 2 Drawing Sheets

OTHER PUBLICATIONS

Ge Liu, Deshan Li, Murali K. Pasumarthy, Tomasz H. Kowalczyk, Christopher R. Gedeon, Susannah L. Hyatt, Jennifer M. Payne, Timothy J. Miller, Peter Brunovskis, Tamara L. Fink, Osman Muhammad, Robert C. Moen, Richard W. Hanson, and Mark J. Cooper, Nanoparticles of Compacted DNA Transfect Postmitotic Cells, article, Jun. 14, 2003, Department of Biochemistry, Case Western Reserve University School of Medicine, Cleveland, Ohio.

X.X. He, K.M. Wang, W.H. Tan, X. Lin, L. Chen and X.H. Chen, A Novel Method For Efficient Gene Delivery Using Amino-Modified Silica Coated Magnetic Nanoparticles, article, Jul. 27, 2003, State Key Laboratory of Chemo/Biosensing and Chemometrics, College of Chemistry & Chemical Engineering, Institute of Biological Science and Biological Technology, Hunan University, P.R. China.

Fadee Mondalek, Concerns Regarding the Permeability of the Round Window Membrane (RWM) to Magnetite Nanoparticles Attached to a Drug/Gene, article, Oct. 28, 2003, OU Health Sciences Center, Oklahoma City, Oklahoma.

Rachel A. Jones, Charles Y. Cheung, Fiona E. Black, Jasmine K. Zia, Patrick S. Stayton, Allan S. Hoffman, and Mark R. Wilson, Poly(2-alkyacrylic acid) polymers deliver molecules to the cytosol by pH-sensitive disruption of endosomal vesicles, article, 2003, Department of Biological Sciences, University of Wollongong, Wollongong, Australia and University of Washington.

Electronic Publication by Business Communications Company, Inc., "Nanoparticle News", issued Oct. 2002.

Christian Plank, Ulrike Schillinger, Franz Scherer, Christian Bergemann, Jean-Serge Remy, Florian Krotz, Martina Anton, Jim Lausier and Joseph Rosenecker, "The Magnetofection method: Using Magnetic Force to Enhance Gene Delivery", Biol. Chem., vol. 384, pp. 737-747, May 2003.

Utreja et al. "Lipoprotein-mimicking biovectorized systems for methotrexate delivery," Pharmaceutica Acta Helvetiae, No. 73 (1999) pp. 275-279 (Abstract XP-002383903).

Schutt et al. "Biocompatible Magnetic Polymer Carriers for In Vivo Radionuclide Delivery," International Society for Artificial Organs, vol. 23, No. 1 (1999) pp. 98-103.

Nicoli et al. "Design of triptorelin loaded nanospheres for transdermal iontophoretic administration," International Journal of Pharmaceutics, No. 214 (2001) pp. 31-35.

Brigger et al. "Nanoparticles in cancer therapy and diagnosis," Advanced Drug Delivery Reviews, vol. 54, (2002) pp. 631-651, Elsevier.

Duclairoir et al. "Alpha-Tocopherol encapsulation and in vitro release from wheat gliadin nanoparticles," J. Microencapsulation, vol. 19 (2002), No. 1, pp. 53-60.

Chang "Adriamycin-loaded immunological magnetic nanoparticles: Site-specific targeting . . . ," Chinese Journal of Biomedical Eng., vol. 15, No. 4 (1996) pp. 354-359, abstract only.

"Magnets Help Target Gene Therapy", Press release, 2002, Bioelectromagnetics Society.

Bruce M. Moskowitz, "Domain Theory", Hitchhiker's Guide to Magnetism, Enviromental Magnetism Workshop, pp. 21-33, Jun. 1991.

"The Basics of Silane Chemistry", A Guide to Silane Solutions from Dow Corning, pp. 7-8, 2005, Dow Corning Corporation.

N. Buske, C. Gansau, T. Rheinlander and B. Kroll, "Magnetic Sizing of Magnetic Nanoparticles",Mediport Kardiotechnik GmBH, 2000.

* cited by examiner

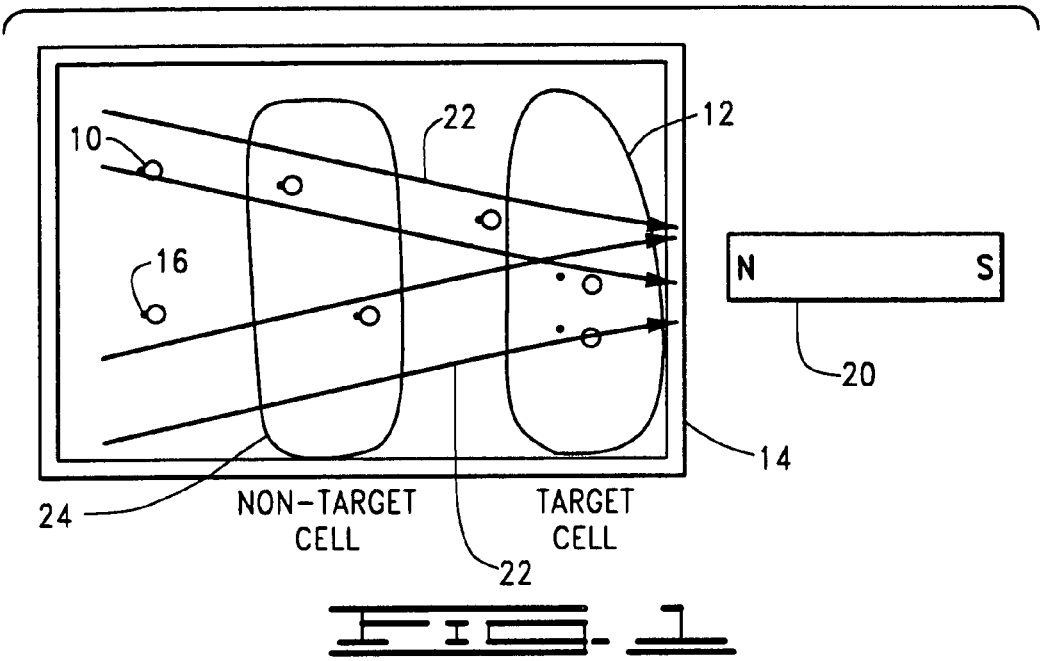
FIG. 1
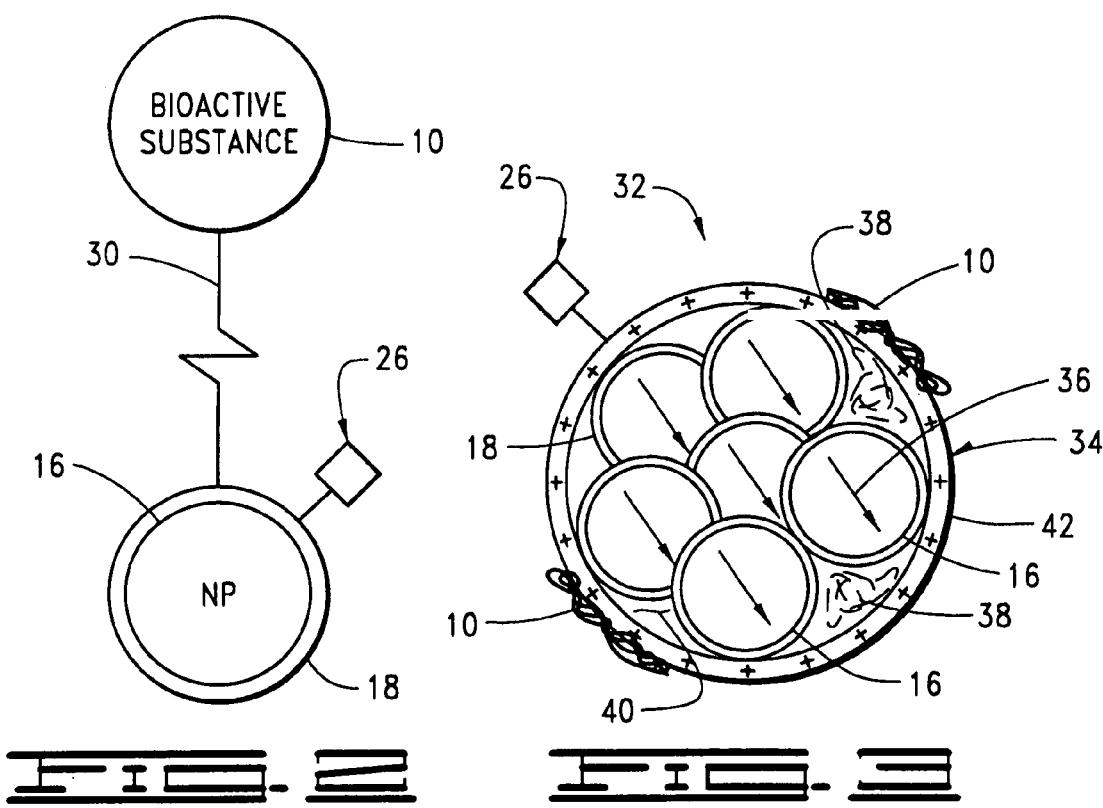
FIG. 2
FIG. 3

DELIVERY OF BIOACTIVE SUBSTANCES TO TARGET CELLS

CROSS REFERENCE TO RELATED APPLICATIONS

This application claims priority of U.S. Provisional Patent Application Ser. No. 60/479,381 filed Jun. 18, 2003.

STATEMENT OF GOVERNMENT INTEREST

This invention was partially funded by the Government under a grant from Naval Medical Center San Diego (NMCSD) under contract NCRADA-NMCSD-03-110. The Government has certain rights to portions of the invention.

FIELD OF THE INVENTION

The present invention relates generally to the delivery of bioactive substances to target cells within a body, and more particularly, to the delivery of genetic material to the inner ear sensory cells of the inner ear using superparamagnetic nanoparticles.

SUMMARY OF THE INVENTION

The present invention is directed to a method of introducing a bioactive substance into a target cell within a body. The bioactive substance is associated with a superparamagnetic nanoparticle. The method comprises introducing the bioactive substance and the nanoparticle into the body and moving the bioactive substance and the nanoparticle into the target cell using a controllable external magnetic field. The controllable external magnetic field is adapted to move the nanosphere in three dimensions.

The present invention further includes a method for introducing a bioactive substance into a target cell within a body wherein the bioactive substance is supported within a nanosphere. The nanosphere comprises at least one superparamagnetic nanoparticle and an outer bioerodable shell. The outer bioerodable shell supports the nanoparticle and the bioactive substance. The method comprises introducing the nanosphere into the body and moving the nanosphere into the target cell using a controllable external magnetic field. The controllable external magnetic field is adapted to move the nanosphere within the body in three dimensions.

Still yet, the present invention includes a system for introducing a bioactive substance into a target cell within a body. The system comprises a superparamagnetic nanoparticle, a biocompatible shell covering the nanoparticle and a magnetic field generator. The biocompatible shell is adapted to bond the bioactive substance with the nanoparticle. The magnetic field generator is adapted to move the nanoparticle to the target cell in three dimensions.

Further still, the present invention includes a method for introducing a bioactive substance into a target cell within a body wherein the bioactive substance is supported within a nanosphere. The nanosphere comprises a superparamagnetic nanoparticle and a bioerodable matrix. The bioerodable matrix supports the nanoparticle and the bioactive substance. The method comprises introducing the nanosphere into the body and moving the nanosphere into the target cell. The nanosphere is moved into the target cell using a controllable magnetic field adapted to move the nanosphere within the body in three dimensions.

BRIEF DESCRIPTION OF THE FIGURES

FIG. 1 is a diagrammatic illustration of the present invention showing the use of a magnetic field to move superparamagnetic nanoparticles and their associated bioactive substance through a non-target cell and into a target cell. FIG. 1 further shows the release of the bioactive substance from the nanoparticle inside the target cell.

FIG. 2 is a diagrammatic illustration of a nanoparticle having a biocompatible shell comprised of silica. The nanoparticle is shown bound to a bioactive substance via a covalent bond.

FIG. 3 is a diagrammatic representation of nanosphere delivery system constructed in accordance with the present invention. The nanosphere of FIG. 3 comprises a plurality of nanoparticles each having a biocompatible shell. The nanoparticles are encapsulated within an outer biocompatible shell. The nanosphere is shown having a bioactive substance comprising a genetic material bonded to the outer biocompatible shell.

DETAILED DESCRIPTION OF THE INVENTION

Figure 4:
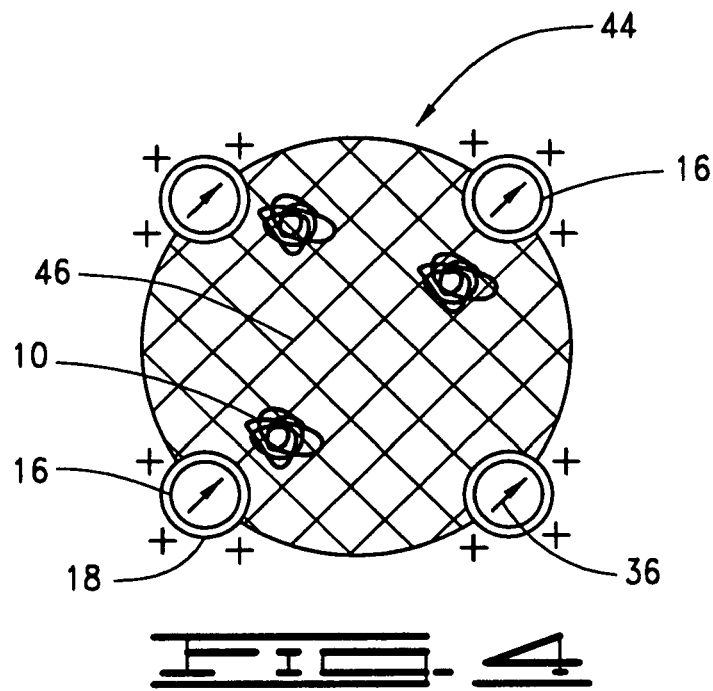
FIG. 4 is a diagrammatic representation of an alternative embodiment of a nanosphere constructed in accordance with the present invention. The nanosphere of FIG. 4 comprises a plurality of silica coated nanoparticles bonded to a bioerodable polymer. The bioerodable polymer is shown supporting a genetic material.

Delivery of bioactive substances, such as drugs or genetic material, to specific cells allows for the treatment of diseases and conditions that affect the human body. Several methods and systems have been developed to accomplish delivery of the bioactive substance. However, there remains an ongoing need for improved delivery methods and systems.

Targeted delivery of bioactive substances using nanospheres and/or nanoparticles to a specific site within a body provides advantages over systemic or oral administration of the bioactive substance to the body. For example, effective doses of bioactive substance may be delivered at varying doses to a desired target cell without exposing the entire body to adverse conditions or side effects. Further, the present method and system allows for the delivery of bioactive substance into sensitive or remote areas of the body in a non-invasive manner using an externally controlled magnetic field adapted to move the nanoparticle in three dimensions.

Viral agents have been used for targeted delivery of genetic material to specific cells within the body. A viral agent that has an affinity for the target cells is chosen to transport the genetic material to the target cells. However, the use of viruses to transport genetic material to specific cells presents difficulties such as infection of the host body, mutation of the virus, and incitement of harmful immunogenic reactions. Additionally, viruses are of such a size that there use may cause damaging trauma to the body by requiring invasive procedures. The present invention is useful in that it minimizes trauma to the body and can use non-immunogenic substances.

Turning now to the drawings in general and FIG. 1 in particular, there is shown therein a system for introducing a bioactive substance 10 into a target cell 12 disposed within a body 14. The bioactive substance 10 is shown bonded to a superparamagnetic nanoparticle 16. The nanoparticle 16 may be covered by a biocompatible shell 18 (FIG. 2) that is adapted to bond the bioactive substance 10 to the nanoparticle 16. A magnetic field generator 20 is positioned outside the body 14 to move the nanoparticles 16 in three dimensions and into the target cell 12.

To move the nanoparticle 16 and the bioactive substance 10 into the target cell 12 the magnetic field generator 20 generates a gradient, represented by arrows 22, which attracts the nanoparticle to the magnetic field generator and into the target cell. The use of a magnetic field gradient 22 facilitates internalization of the nanoparticle 16 and bioactive substance 10 by the target cell 12. Facilitating uptake of the nanoparticle 16 and bioactive substance 10 using the magnetic field generator may prevent premature release of the bioactive substance from the nanoparticle. Once the nanoparticle 16 and bioactive substance 10 are moved into the target cell 12, the bond between them is broken and the bioactive substance may be released.

The magnetic field generator 20 may comprise a plurality of magnets (not shown) that are arranged such that a magnetic field is generated, within which numerous gradients 22 may be created to three-dimensionally direct the nanoparticles 16 to the target cell 12. An alternative magnetic field generator may comprise an electromagnetic field generating coil that is movable in three dimensions and adapted to create a gradient 22 that moves the nanoparticle 16 through a non-target cell 24 and into the target cell 12. It will be appreciated that the electromagnetic field generating coil may be moved by any means that permits three-dimensional movement of the nanoparticle 16 through the body 14. In a preferred embodiment the electromagnetic field generating coil may be supported on the end of a robotic arm (not shown) that is programmed to move around the body 14 so that the nanoparticle 16 is directed in three dimensions to the target cell 12.

Turning now to FIG. 2, there is shown therein the nanoparticle 16 and bioactive substance 10 of FIG. 1 covalently bonded to one another. The nanoparticle 16 may be comprised of a ferrite such as magnetite and is preferably superparamagnetic. Because the nanoparticles 16 are superparamagnetic, the nanoparticles will only be attracted to the strongest side of the magnetic field gradient 22 and will not be attracted by other or similar nanoparticles when in a magnetic field. Thus, particle to particle interactions resulting in aggregation or other undesirable effects are minimized. Once the magnetic field is removed, the nanoparticles 16 lose their magnetic remanence.

The nanoparticle 16 of FIG. 2 is shown encapsulated in a biocompatible shell 18. In a preferred embodiment of the present invention the biocompatible shell 18 may comprise silica ($SiO_2$) or titania ($TiO_2$). Encapsulation of the nanoparticle 16 in the biocompatible shell 18 hermetically seals the nanoparticle to help prevent corrosion of the nanoparticle and provides a surface charge to promote suspension of the nanoparticle in solution to facilitate uptake of the nanoparticle by non-target 24 and target cells 12. The biocompatible shell 18 also provides a substrate for the attachment of amines 26 that can serve as linkers to other molecules. The biocompatible shell 18 of FIG. 2 is shown to provide a covalent bond 30 such as a Sulfhydryl bond between the bioactive substance 10 and the nanoparticle 16.

Turning now to FIG. 3, there is shown therein a diagrammatic representation of a nanosphere 32 prepared using the methods and systems described in co-pending U.S. patent application Ser. No. 10/724,563, the contents of which are incorporated herein by reference. The nanosphere 32 of FIG. 3 comprises a plurality of superparamagnetic nanoparticles 16 supported within the nanosphere by an erodable polymer matrix (not shown). Each nanoparticle 16 may be encapsulated within the previously described biocompatible silica shell 18. The nanosphere 32 has an outer shell 34 that may be adapted to support the bioactive substance 10. The nanosphere generally has a diameter of less than 300 nanometers, and more preferably a diameter of 100 nanometers or less.

The nanoparticles 16 may be arranged within the outer shell 34 such that they have uniformly aligned magnetic moments 36. Uniform alignment of the nanoparticles' magnetic moments 36 increases the magnetic susceptibility of the nanosphere 32 thus providing more efficient transport of the nanosphere and the bioactive substance 10 through the body 14 and into the target cell 12.

The outer shell 34 generally encapsulates the nanoparticle 16 and provides a support mechanism for the bioactive substance 10 so that it may be transported with the nanoparticles to the target cell 12. In one embodiment the outer shell 34 may comprise a bioerodable polymer that is adapted to release an encapsulated bioactive substance 38. In this embodiment, the outer bioerodable shell 34 may comprise any erodable synthetic or natural polymer that is biocompatible. Polylactides, polyglycolides and collagen have been found to be acceptable for use as the outer bioerodable shell 34 of the nanosphere 32.

If the outer shell 34 comprises a bioerodable polymer, the nanosphere 32 may form a reservoir 40 that encapsulates the bioactive substance 38 and the nanoparticles 16 within the nanosphere. As the outer shell 34 is dissolved, the bioactive substance 38 is released from the nanosphere 32 and dispersed into the cytoplasm (not shown) of the target cell 12. The inclusion of the erodable polymer matrix further aids in regulating release of the bioactive substance 38.

Continuing with FIG. 3, the bioerodable polymer matrix may be used to entrap the bioactive substance 38 within the outer bioerodable shell 38. As the outer bioerodable shell 34 and the erodable matrix dissolve the bioactive substance 38 is released at a rate dependent upon dissolution of the outer shell and the matrix. Thus, it is preferable that the erodable polymer matrix is non-toxic and capable of being consumed, metabolized or expelled by the target cell 12. (FIG. 1.) An example of such an erodable polymer matrix is collagen. A tightly cross-linked matrix will exhibit a slow release rate providing low doses of bioactive substance 38 over longer periods of time. When no bioerodable matrix is present rapid release of the bioactive substance 38 can be expected.

Continuing with FIG. 3, the bioactive substance 10 may alternatively be supported on the outer shell 34. In such cases the outer shell 34 may be formed from either the bioerodable polymer or a biostable polymer. By way of example, the outer shell 34 of the nanosphere 32 may comprise a silica matrix. The silica matrix may have a plurality of amine groups 26 attached to the outer surface 42 of the outer shell 34 that functionalize the nanosphere 32. These amine groups 26 give the outer surface 42 of the shell 34 a net positive charge. A positively charged outer shell 34 has an affinity for bioactive substance 10 comprising genetic material that has a generally negative net charge.

It will be appreciated that the bioactive substance 10 or 38 may itself form the outer shell by attaching the bioactive substance directly to the silica coated nanoparticles 16 or alternatively to the previously described silica matrix.

The outer shell 34 of the nanosphere 32 may have a cell adhesion factor (not shown) supported on the outer surface 42 of the shell 34. The use of cell adhesion factors enhances endocytosis of the bioactive substance 10 or 38 supported by the nanosphere 32 by the target cell 12. (FIG. 1.) Thus, the cell adhesion factor may comprise a protein having an affinity for a predetermined type of cell. It will be appreciated that a wide array of cell adhesion factors may be used with nanospheres 32 of the present invention without departing from the spirit of the invention.

Turning now to FIG. 4, there is shown therein an alternative nanosphere 44 of the present invention that may be used to deliver the bioactive substance 10 to the target cell 12. The nanosphere 44 of FIG. 4 comprises a plurality of superparamagnetic nanoparticles 16 supported by a bioerodable polymer matrix 46. In the present embodiment, the nanoparticles 16 are shown with the biocompatible shell 18. The nanoparticles 16 may be supported by the bioerodable polymer matrix 46 so that they have substantially aligned magnetic moments 36. The bioactive substance 10 is likewise supported by the bioerodable polymer matrix 46 so that the amount of bioactive substance 10 released from the nanosphere 44 and into the target cell 12 may be controlled over time.

Figure 5:
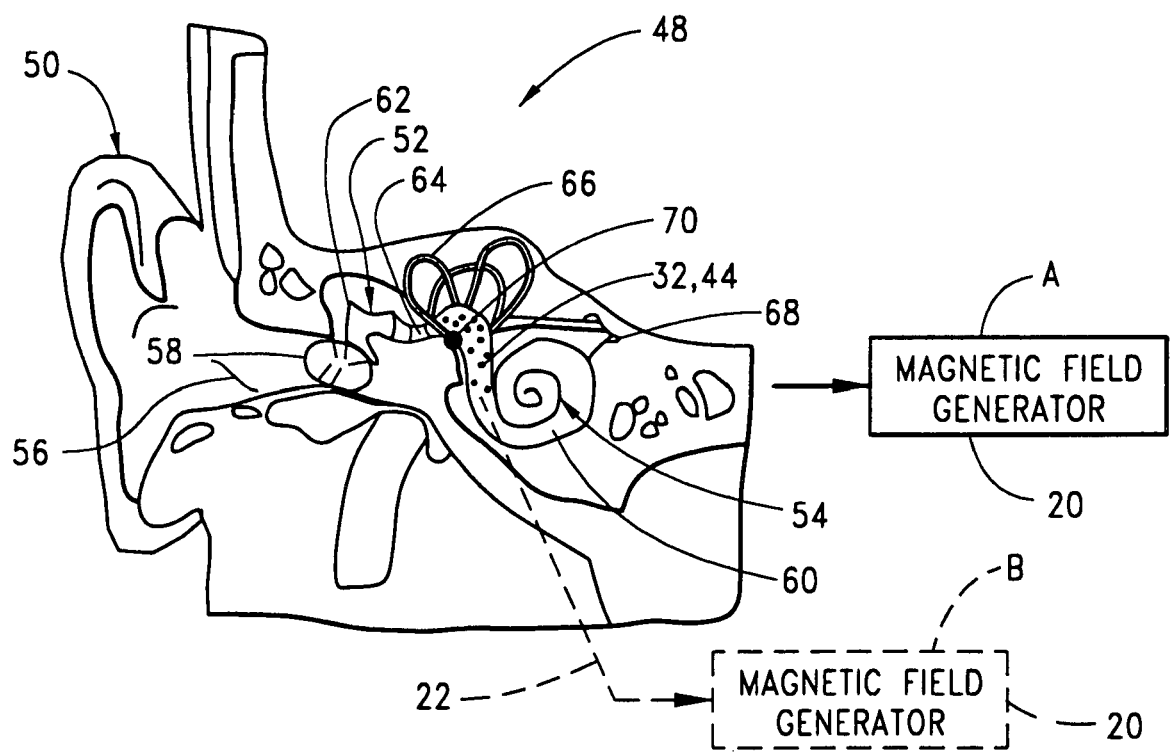
FIG. 5 is an illustration of a human ear showing the movement of nanospheres through the round window membrane and into the inner ear. The magnetic field generator is shown in a plurality of positions to illustrate guided movement of the nanospheres by moving the magnetic field generator.

Turning now to FIG. 5, there is shown therein an illustration of a human ear 48. The ear 48 shown in FIG. 5 comprises an outer ear 50, a middle ear 52 and an inner ear 54. The outer ear 50 has an ear canal 56 that is closed at one end by a tympanic membrane 58, or eardrum. The middle ear comprises an ossicular chain that normally connects the ear drum 58 to a cochlea 60. The ossicular chain includes a malleus 62, an incus 64, and a stapes 66. A properly functioning ossicular chain transmits and amplifies sound vibrations from the ear drum 58 through the malleus 62, incus 64 and stapes 66 to vibrate an oval window (not shown) of the inner ear 54. Vibration of the oval window is transmitted to the fluid of the inner ear to cause movement of ear sensory cells within the cochlea 60 of the inner ear 54. Electrical impulses from the ear sensory cells are sent from the cochlea 60 along an auditory nerve 68 to the brain of the mammal where the signals are processed for hearing.

Damage to the ear sensory cells, or hair cells, of the cochlea 60 is the leading cause of sensorineural hearing loss. Congenital conditions and/or exposure to injurious levels of noise may be the cause of damage to the hair cells. After the hair cells are initially damaged, a number of inner ear cell death programs are activated that result in eventual hair cell death and permanent hearing loss. However, the supporting cells may remain alive with the capacity to regenerate hair cells and restore hearing when triggered by the appropriate bioactive substance 10.

FIG. 5 illustrates a method of moving magnetically responsive nanospheres 32 or 44, as described herein, into the inner ear 54 for regeneration or repair of hair cells. Nanosphere 32 is used herein for illustration purposes, it will be appreciated that nanospheres having different constructions and configurations and individual nanoparticles 16 as previously described herein may be used to treat the target cells without departing from the spirit of the invention. The nanospheres 32 are placed near the round window membrane 70 of the inner ear 54 and pulled through the round window membrane using the gradient 22 generated by the magnetic field generator 20 in position A. Once inside the cochlea 60, the nanospheres 32 are moved is three dimensions through the perilymph to hair cell supporting cells using the external magnetic field generator 20. The diagrammatic magnetic field generator 20 is shown, in FIG. 5, in an alternative position B to facilitate movement of the nanosphere 32 through the basal turn 72 of the cochlea 60.

When the nanosphere reaches the hair cell supporting cell, the magnetic field generator 20 may be moved to an alternative position to facilitate magnetofection of the nanosphere into the cell. Once inside the hair cell supporting cell, the bioactive substance 10 is released into the cytoplasm of the target cell to begin repair or regeneration of the hair cells. The bioactive substance 10 released into the hair cells may comprise a genetic material such as the Hath-1 gene. The Hath-1 gene has been shown to stimulate regeneration of hair cells in mammals. See, "Robust Generation of New Hair Cells in the Mature Mammalian Inner Ear by Adenovirus Expression of Hath-1," J. Shou, J. L. Zheng, W. Q. Gao, Molecular and Cellular Neuroscience 2003; 23:169-170, the contents of which are incorporated herein by reference.

The present invention also comprises a method for introducing a bioactive substance 10 into a target cell 12 within a body 14. The bioactive substance 10 is generally associated with a superparamagnetic nanoparticle 16. The bioactive substance 10 is introduced into the target cell 12 by introducing the bioactive substance and the nanoparticle 16 into the body 14 and moving the bioactive substance into the target cell. The bioactive substance 10 is moved into the target cell 12 using an externally controlled magnetic field that is adapted to move the nanoparticle 16 and bioactive substance through the body 14 and any non-target cells 24. Movement of the nanoparticle 16 may comprise generating a gradient 22 in the external magnetic field. Preferably one of the nanoparticles 16 or nanospheres 32 or 44 as described herein may be used for this purpose.

In accordance with the method of present invention, the bioactive substance 10 may comprise genetic materials, such as DNA, RNA, plasmids, oligonucleotides or proteins, which are bonded to the biocompatible silica shell 18 that covers the nanoparticle 16. The bond between the genetic material 10 and the silica shell 18 is adapted to release the genetic material after the nanoparticle 16 and genetic material are pulled into the target cell 12.

In an exemplary application of the present method, the body 14 may comprise a mammal having a target cell 12 disposed within the cochlea 60 of the mammal's ear 50. Thus, the externally controlled magnetic field may be used to move the genetic material 10 and nanoparticle 16 into the cochlea 16, then to disperse the genetic material throughout the cochlea and across the cellular membrane (not shown) of the ear sensory cells. Once inside the target ear sensory cell 12, the genetic material may be released from the nanoparticle 16 or nanosphere 32. The genetic material 10 may then transfect the ear sensory cell or the supporting cell to cause repair or regeneration of the cells.

EXAMPLE PROCEDURE

Superparamagnetic nanoparticles having a silica shell were synthesized using the modified Massart procedures described in co-pending U.S. patent application Ser. No. 10/724,563. The nanoparticles were made of magnetite ($Fe_3O_4$) and synthesized to have a diameter of less than 30-50 nanometers. A two Molar iron (III) sulfate heptahydrate solution was prepared in two (2) Molar HCl and combined with one Molar iron (III) chloride hexahydrate aqueous solution. The solutions were mixed and washed in a 0.7 Molar ammonium hydroxide solution and rapidly stirred. The resulting precipitate was stirred for thirty (30) minutes then collected using a magnet. After multiple washes, the precipitate was re-suspended in 0.7 Molar ammonium hydroxide and peptized by the addition of one (1) Molar tetramethylammonium hydroxide aliquots. The volume of the resulting suspension was then taken to 250 ml for processing to add the silica shell to the nanoparticles.

To confirm the iron oxide phase and size of the magnetic nanoparticle, several uncoated magnetite particles were characterized using X-ray diffraction (XRD). XRD analysis revealed the presence of magnetite particles having an average diameter of ten (10) nanometers. The diameter of the magnetite particles was confirmed using Transmission Electron Microscopy (TEM). Further observation of the uncoated magnetite particles using High Resolution Transmission Electron Microscopy further established the existence of magnetite particles.

Encapsulation of the nanoparticle with silica provides an anionic surface charge that promotes endocytosis as well as a substrate for attachment of amines adapted to link the bioactive substance to the nanoparticle. The suspension of magnetite nanoparticles was stirred and a 4 ml aliquot was taken up to 100 ml with distilled water. A solution of 0.54% sodium silicate was prepared at a pH of 10.5, and 4 ml of the sodium silicate was added to the magnetite nanoparticle suspension. The pH of the resulting suspension was adjusted to 10.0 and stirred for an extended period of time. After settling for several hours, the silica-coated nanoparticles were removed from the excess silica using a magnet to pull the particles out of the solution and by washing the precipitate several times with distilled water.

Several of the silica-coated nanoparticles were analyzed using TEM to determine the size and structure of the nanoparticles produced in the above procedure. Analysis of the coated nanoparticles revealed an average diameter of approximately sixteen (16) nanometers with a standard deviation of 2.3 nanometers. The presence of the silica shell and iron oxide core was confirmed by energy-dispersive X-ray spectrometry ("EDS").

Silica-coated nanoparticles were then functionalized by the addition of amine groups to the surface of the silica shell. The nanoparticles were treated with 3-aminopropyl trimethoxy silane and a 1 ml aliquot of the resulting suspension was brought to a volume of 5 ml with distilled water. Additional 3-aminopropyl trimethoxy silane was added to the suspension to bring the final concentration to five percent (5%). The reaction system was stirred and the resulting nanoparticles were washed and collected. A Kaiser assay was performed on several of the functionalized nanoparticles to confirm the presence of amine groups on the surface of the silica-coated nanoparticles.

Fluorescein isothiocyanate (FITC) was used to label the nanoparticle for subsequent location of the nanoparticle using confocal microscopy. The particles were conjugated with FITC using standard protocols to attach the FITC to the amine functional groups.

Guinea pigs were anesthetized and positioned such that an experimental ear was facing upward and parallel to the operating table. A retro-articular incision was made to expose the temporal bone over the middle ear cavity. The middle ear space was opened using an otological surgical drill system (MicroCraft™, Xomed Inc., Jacksonville, Fla.) to expose the ossicular chain of the subjects.

The silica-coated magnetic nanoparticles were suspended in saline at a pH of 7.4 and sonicated for several minutes. Sonication was performed to disperse the nanoparticles before placement onto the ossicular epithelium. A volume of 50-75 microliters of the nanoparticle suspension was applied to the target cells in 25 microliter doses. The operative site was closed and the subjects recovered during application of an external magnetic field to the their heads.

An externally vectored magnetic force was applied to the heads of the experimental animals using an external magnet so that the nanoparticles were pulled downward into the epithelia of the incus and tympanic membrane. The magnet created a magnetic field of approximately 0.35 Tesla at one inch from the experimental incus and tympanic membrane. Each subject was exposed to the external magnetic field for 20 to 30 minutes and subsequently monitored for survival for several days.

Eight to fifteen days after surgery the subjects were anesthetized and euthanized. The experimental incus and tympanic membrane were dissected and prepared for observation. Confocal laser and epifluorescence microscopy were used to confirm the delivery of FITC-labeled nanoparticles into the epithelia of the incus and tympanic membrane. Florescence within the target cells of the incus and the tympanic membrane confirmed that the FITC-labeled nanoparticles had been internalized by the target epithelial cells of the incus and tympanic membrane. Control specimens, not subjected to the external magnetic field, showed reduced intracellular fluorescence showing that the external magnetic field facilitated internalization of the FITC-labeled nanoparticles by the target cells.

Various modifications can be made in the design and operation of the present invention without departing from the spirit thereof. Thus, while the principal preferred construction and modes of operation of the invention have been explained in what is now considered to represent its best embodiments, which have been illustrated and described, it should be understood that within the scope of the appended claims, the invention may be practiced otherwise than as specifically illustrated and described.

What is claimed is:

1. A system for introducing a bioactive substance into a target cell within a body, the system comprising:
    a nanosphere comprising
        a plurality of superparamagnetic nanoparticles contained within a single outer shell layer; and
        a biocompatible shell covering each nanoparticle, wherein the biocompatible shell is adapted to bond the bioactive substance with the nanoparticle; and
    a magnetic field generator adapted to move the nanoparticle in three dimensions to the target cell.

2. The system of claim 1 wherein the magnetic field generator comprises a plurality of magnets arranged external to the body such that a three-dimensional magnetic field is generated.

3. The system of claim 1 wherein the nanoparticle comprises magnetite.

4. The system of claim 1 wherein the bioactive substance comprises a genetic material.

5. The system of claim 1 wherein the biocompatible shell comprises silica.

6. The system of claim 1 wherein the outer shell comprises a bioerodable substance that releases the bioactive substance from the nanosphere.

7. The system of claim 1 wherein the plurality of superparamagnetic nanoparticles have uniformly aligned magnetic moments.

8. The system of claim 1 wherein the outer shell comprises a polyglycolide.

9. The system of claim 1 wherein the magnetic field generator comprises an electromagnetic coil that is movable in three dimensions and adapted to create a gradient that moves the nanoparticle into the target cell.

10. The system of claim 1 further comprising amine groups carried by the biocompatible shell of the nanoparticle, wherein the bioactive substance is bonded to the amine groups.

11. A system for introducing a bioactive substance into a target cell within a body, the system comprising:
a nanosphere comprising
the bioactive substance;
a plurality of superparamagnetic nanoparticles;
a biocompatible shell covering each nanoparticle; and
a single bioerodable outer shell layer encapsulating the plurality of superparamagnetic nanoparticles; and
a magnetic field generator adapted to move the nanosphere in three dimensions to the target cell.

12. The system of claim 11 wherein the bioerodable outer shell is selected to bond the bioactive substance.

13. The system of claim 11 wherein the bioerodable outer shell encapsulates the bioactive substance.

14. The system of claim 11 wherein the nanoparticle comprises magnetite.

15. The system of claim 11 wherein the magnetic field generator comprises a plurality of magnets arranged external to the body such that a three-dimensional magnetic field is generated.

16. The system of claim 11 wherein the magnetic field generator comprises an electromagnetic field generating coil that is movable in three dimensions and adapted to create a gradient that moves the nanoparticle into the target cell.

17. The system of claim 11 wherein the plurality of superparamagnetic nanoparticles have uniformly aligned magnetic moments.

18. The system of claim 1, further comprising a cell adhesion factor supported on an outer surface of the single outer shell layer.

19. The system of claim 11, further comprising a cell adhesion factor supported on an outer surface of the single bioerodable outer shell layer.

* * * * *